United States Patent
Kampa et al.

(10) Patent No.: US 10,751,510 B2
(45) Date of Patent: Aug. 25, 2020

(54) SLIDING DISTAL COMPONENT ASSEMBLY

(71) Applicant: IMRICOR MEDICAL SYSTEMS, INC., Burnsville, MN (US)

(72) Inventors: Nicholas J. Kampa, Eagan, MN (US); Scott Kimmel, Roseville, MN (US)

(73) Assignee: Imricor Medical Systems, Inc., Burnsville, MN (US)

( * ) Notice: Subject to any disclaimer, the term of this patent is extended or adjusted under 35 U.S.C. 154(b) by 150 days.

(21) Appl. No.: 15/771,303

(22) PCT Filed: Oct. 28, 2016

(86) PCT No.: PCT/US2016/059299
§ 371 (c)(1),
(2) Date: Apr. 26, 2018

(87) PCT Pub. No.: WO2017/075336
PCT Pub. Date: May 4, 2017

(65) Prior Publication Data
US 2018/0311471 A1    Nov. 1, 2018

Related U.S. Application Data

(60) Provisional application No. 62/247,525, filed on Oct. 28, 2015.

(51) Int. Cl.
*A61M 25/01* (2006.01)
*A61B 10/06* (2006.01)
(Continued)

(52) U.S. Cl.
CPC ......... *A61M 25/0147* (2013.01); *A61B 10/06* (2013.01); *A61B 17/3421* (2013.01);
(Continued)

(58) Field of Classification Search
CPC . A61B 10/06; A61B 17/29; A61B 2017/2939; A61B 2017/2932; A61B 34/71
See application file for complete search history.

(56) References Cited

U.S. PATENT DOCUMENTS 7,824,401 B2 * 11/2010 Manzo ............... A61B 18/1442
606/41
8,333,780 B1 * 12/2012 Pedros ................ A61B 17/29
600/37
(Continued)

FOREIGN PATENT DOCUMENTS

WO    WO-2010/126129 A1    11/2010
WO    WO-2015/088647 A1    6/2015

OTHER PUBLICATIONS

Extended European Search Report, issued by the European Patent Office, regarding corresponding patent application Serial No. EP16860867.7, dated May 6, 2019, 7 pages.
(Continued)

*Primary Examiner* — Tan-Uyen T Ho
*Assistant Examiner* — Lee O Chedister
(74) *Attorney, Agent, or Firm* — Fox Rothschild LLP

(57) ABSTRACT

A sliding distal component assembly for use in medical catheters, bioptomes and other medical devices is provided. The sliding distal component assembly includes a tubular shaft having a lumen, the tubular shaft coupled to an actuation mechanism moveable between a first position and a second position. A tip support is coupled to the tubular shaft and defines a tip support cavity therewithin. The sliding component assembly includes a pulley system having at least one pulley, a sliding distal component and at least one pull wire coupled to the pulley and the sliding distal component with at least a portion of said pulley system being housed within said tip support cavity. When the actuation mechanism is in the first position the sliding distal
(Continued)

component is configured to translate proximally and when the actuation mechanism is in the second position the sliding distal component is configured to translate distally.

19 Claims, 10 Drawing Sheets

(51) Int. Cl.
    *A61B 17/34*     (2006.01)
    *A61B 10/02*     (2006.01)

(52) U.S. Cl.
    CPC ............... *A61B 2010/0208* (2013.01); *A61M 2025/015* (2013.01)

(56) References Cited

U.S. PATENT DOCUMENTS

| | | | |
|---|---|---|---|
| 9,937,626 B2* | 4/2018 | Rockrohr | B25J 15/0226 |
| 2005/0240178 A1* | 10/2005 | Morley | A61B 18/1445 606/51 |
| 2013/0184642 A1* | 7/2013 | O'Donnell | A61M 25/0097 604/95.04 |
| 2015/0032119 A1 | 1/2015 | Kuroda et al. | |

OTHER PUBLICATIONS

International Search Report and Written Opinion, issued by the United States Receiving Office, regarding corresponding international patent application Serial No. PCT/US2016/059299, dated Jan. 3, 2017; 10 pages. USA.

* cited by examiner

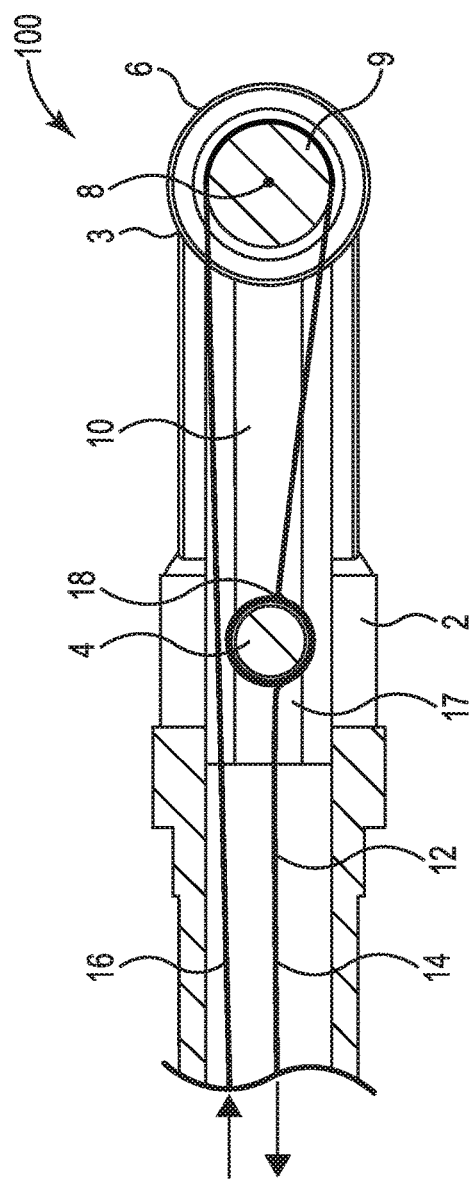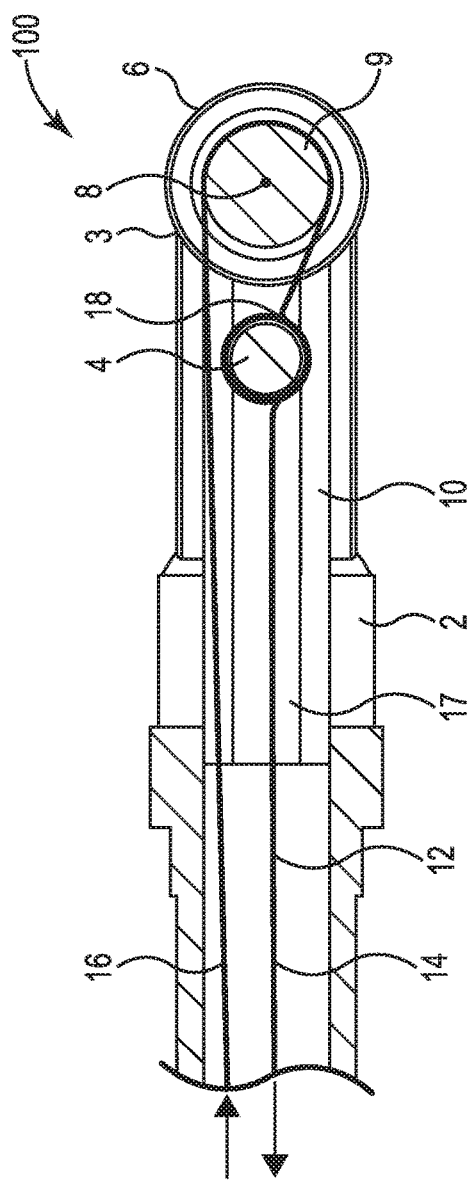

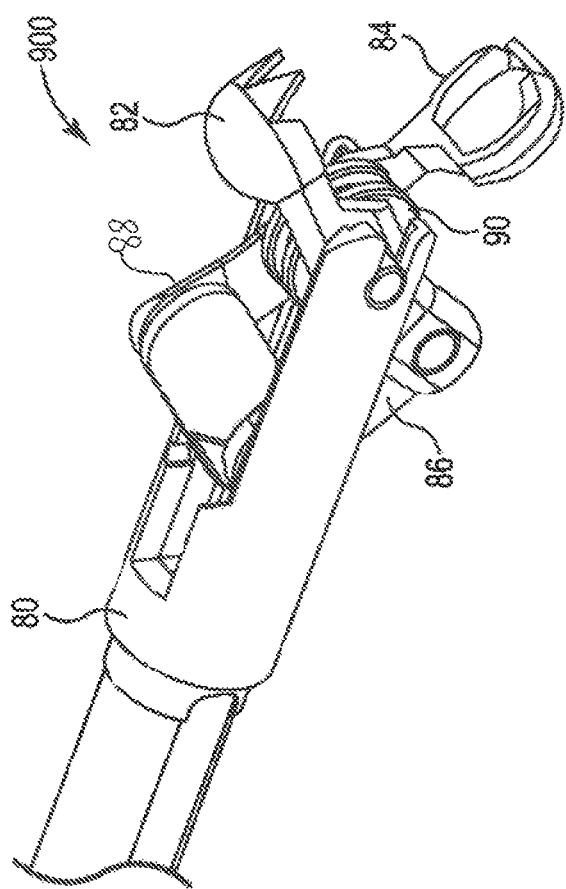

SLIDING DISTAL COMPONENT ASSEMBLY

CROSS REFERENCE TO RELATED APPLICATIONS

This application is national stage patent application of International patent application Serial No.: PCT/US2016/059299, filed on Oct. 28, 2016; which claims the benefit of U.S. Provisional patent application Ser. No. 62/247,525, filed on Oct. 28, 2015; the entireties of which are hereby incorporated by reference.

FIELD OF THE INVENTION

This invention relates to a sliding distal component assembly for use in medical catheters, bioptomes and other medical devices.

BACKGROUND OF THE INVENTION

Traditionally, deflectable medical catheters have been used in interventional procedures to deliver therapies, such as RF energy, or implantables, such as leads or valves, into the body. Medical catheters have also been used for imaging and diagnostic purposes. Finally, medical catheters, such as those with balloons, have been used to modify a patient's anatomy, such as during a structural heart application. In many cases, the aforementioned applications of medical catheters could benefit from the integration of MRI.

MRI has achieved prominence as a diagnostic imaging modality, and increasingly as an interventional imaging modality. The primary benefits of MRI over other imaging modalities, such as X-ray, include superior soft tissue imaging and avoiding patient exposure to ionizing radiation produced by X-rays. MRI's superior soft tissue imaging capabilities have offered great clinical benefit with respect to diagnostic imaging. Similarly, interventional procedures, which have traditionally used X-ray imaging for guidance, stand to benefit greatly from MRI's soft tissue imaging capabilities. In addition, the significant patient exposure to ionizing radiation associated with traditional X-ray guided interventional procedures is eliminated with MRI guidance.

A variety of MRI techniques are being developed as alternatives to X-ray imaging for guiding interventional procedures. For example, as a medical device is advanced through the patient's body during an interventional procedure, its progress may be tracked so that the device can be delivered properly to a target site. Once delivered to the target site, the device and patient tissue may be monitored to improve therapy delivery. Thus, tracking the position of medical devices is useful in interventional procedures. Exemplary interventional procedures include, for example, cardiac electrophysiology procedures including diagnostic procedures for diagnosing arrhythmias and ablation procedures such as atrial fibrillation ablation, ventricular tachycardia ablation, atrial flutter ablation, Wolfe Parkinson White Syndrome ablation, AV node ablation, SVT ablations and the like. Tracking the position of medical devices using MRI is also useful in oncological procedures such as breast, liver and prostate tumor ablations; and urological procedures such as uterine fibroid and enlarged prostate ablations.

MRI uses three fields to image patient anatomy: a large static magnetic field, a time-varying magnetic gradient field, and a radiofrequency (RF) electromagnetic field. The static magnetic field and time-varying magnetic gradient field work in concert to establish both proton alignment with the static magnetic field and also spatially dependent proton spin frequencies (resonant frequencies) within the patient. The RF field, applied at the resonance frequencies, disturbs the initial alignment, such that when the protons relax back to their initial alignment, the RF emitted from the relaxation event may be detected and processed to create an image.

Each of the three fields associated with MRI presents safety risks to patients when a medical device is in close proximity to or in contact either externally or internally with patient tissue. One important safety risk is the heating that may result from an interaction between the RF field of the MRI scanner and the medical device (RF-induced heating), especially medical devices that have elongated conductive structures, such as braiding and pull-wires in catheters and sheaths.

The RF-induced heating safety risk associated with elongated metallic structures in the MRI environment results from a coupling between the RF field and the metallic structure. In this case several heating related conditions exist. One condition exists because the metallic structure electrically contacts tissue. RF currents induced in the metallic structure may be delivered into the tissue, resulting in a high current density in the tissue and associated Joule or Ohmic tissue heating. Also, RF induced currents in the metallic structure may result in increased local specific absorption of RF energy in nearby tissue, thus increasing the tissue's temperature. The foregoing phenomenon is referred to as dielectric heating. Dielectric heating may occur even if the metallic structure does not electrically contact tissue, such metallic braiding used in a deflectable sheath. In addition, RF induced currents in the metallic structure may cause Ohmic heating in the structure, itself, and the resultant heat may transfer to the patient. In such cases, it is important to attempt to both reduce the RF induced current present in the metallic structure and/or eliminate it all together by eliminating the use of metal braid and long metallic pull-wires.

The static field of the MRI will cause magnetically induced displacement torque on any device containing ferromagnetic materials and has the potential to cause unwanted device movement. It is important to construct the catheter shaft and control handle from non-magnetic materials, to eliminate the risk of unwanted device movement.

When performing interventional procedures under MRI guidance, clinical grade image quality must be maintained. Conventional deflectable catheters are not designed for MRI and may cause image artifacts and/or distortion that significantly reduce image quality. Constructing the catheter from non-magnetic materials and eliminating all potentially resonant conductive structures allows the catheter to be used during active MR imaging without impacting image quality. Similarly, it is as important to ensure that the catheter control handle is also constructed from non-magnetic materials thereby eliminating potentially resonant conductive structures that may prevent the control handle being used during active MR imaging.

In many medical procedures in which a catheter is utilized, there is a need for the integration of a sliding component in the distal section of the catheter. Such a sliding component would translate distally and proximally within a distal tip section of the catheter. In conventional sliding distal component assembly designs, translation of the sliding distal component is achieved by pulling or pushing on a stiff rod that is coupled to the sliding distal component. The presence of a stiff rod or cable makes a catheter less flexible, and therefore is not ideal for catheters that are used to navigate tortuous anatomy. In addition, if the catheter or cable is a smaller size, such as 7 Fr or less, there would not be sufficient space in the lumen of the catheter for the stiff rod. This problem necessitates that the rod or cable be smaller than the internal diameter of the catheter. In addition, it necessitates that the rod or cable comprise a metallic composition because metal is the most suitable material for creating a small rod that has acceptable column strength to push the sliding distal component.

For the foregoing reasons, such a long metal rod or cable should not be utilized in those cases in which MRI guidance is employed. Thus, what is needed is an MR compatible sliding distal component mechanism design that could be universally used with both large and small catheters alike.

BRIEF SUMMARY OF THE INVENTION

The foregoing need is addressed by the sliding distal component assembly in accordance with this invention. In one aspect of the invention, the sliding distal component assembly includes a pulley system including a pull wire to impart axial movement to a sliding distal component. The pulley system broadly includes the sliding distal component, one or more pulleys, one or more pull wires, and a tip support. The tip support defines a cavity that may house the pulley system, completely or partially, and is positioned at the distal end of a catheter. The sliding distal component may also include a pin or keying feature that is configured to engage with internal mating features within the cavity of the tip support and is configured to allow the sliding distal component to translate proximally or distally in relation to the longitudinal axis of the tip support. In one aspect the pulley may be coupled to the distal end of the tip support and extends outwardly therefrom. The pulley is configured to rotate freely but does not translate. The catheter includes a lumen that extends along the entire length of the catheter body. At the distal end of the catheter, the tip support is coupled to the catheter such that the tip support cavity and catheter lumen form a continuous channel.

In other aspects of the invention, the pulley may be coupled to the distal end of the tip support and is housed within the tip support cavity and may be offset from the longitudinal axis of the tip support. In other aspects of the invention one or more pulley may be utilized.

In one aspect of the invention, the pull wire is a single pull wire having a first section and a second section. The first section of the pull wire originates proximally from the catheter lumen and is operably coupled to actuation means, such as a pull trigger, slide button, etc., and extends distally into the tip support cavity, where it is wound around and coupled to the sliding distal component at a fixation point. The coupling at the fixation point may be a mechanical coupling such as by welding or soldering or may be a chemical coupling such as chemical bonding or adhesive. Those of skill in the art will appreciate that the coupling may be at a single point or may extend partially or wholly around the circumference of the sliding distal component. The second section of the pull wire extends distally from the fixation point at the sliding distal component and wound around the pulley. The second section then extends proximally and routed through the tip support cavity without contacting the sliding distal component and through the catheter lumen to the proximal end of the catheter where it may be coupled to actuation means such as a pull trigger, slide button, or other mechanisms known to those of skill in the art.

When actuated the sliding distal component may translate in both the proximal and distal directions by actuating the proximal end of the first or second pull wire sections. In other words, the sliding distal component does not have to be pushed to be translated in the proximal or distal direction. Pull wires, on the other hand, can have a small diameter (smaller than a metallic rod), and yet be made of non-metallic materials, such as KEVLAR (poly-para-phenylene terephthalamide). Numerous applications exist in which it may be desirable to have an extendable and retractable mechanism located at the tip of a catheter. Example applications include the delivery of an implantable device or medication, or the puncturing of target tissue for diagnostic or therapeutic purposes.

Other aspects of the invention are found in the following numbered clauses:

1. A sliding distal component assembly including a tubular shaft having a lumen, the tubular shaft coupled to an actuation mechanism moveable between a first position and a second position; a tip support operably coupled to said tubular shaft and defining a tip support cavity therewithin, said tip support cavity continuous with said tubular shaft lumen; a pulley system including at least one pulley, a sliding distal component and at least one pull wire operably coupled to said pulley and said sliding distal component, at least a portion of said pulley system being housed within said tip support cavity, wherein when said actuation mechanism is in said first position the sliding distal component is configured to translate proximally and when said actuation mechanism is in said second position the sliding distal component is configured to translate distally.

2. The sliding distal component assembly of clause 1 wherein said at least one pull wire further comprises a first pull wire section having a distal end coupled to said sliding distal component at a fixation point and a proximal end coupled to said actuation mechanism and a second pull wire section having a distal end coupled to said fixation point and a proximal end coupled to said actuation mechanism, wherein said second pull wire section is operably coupled to said at least one pulley.

3. The sliding distal component assembly of clause 2 wherein said actuation mechanism is configured in the first position to apply tension to the proximal end of the first pull wire section to cause said sliding distal component to translate proximally and further wherein said actuation mechanism is configured in the second position to apply tension to the proximal end of the second pull wire section to cause said sliding distal component to translate distally.

4. The sliding distal component assembly of clause 1 wherein said tip support cavity including a pair of opposing channels therewithin for slidably receiving said sliding distal component.

5. The sliding distal component assembly of clause 1 wherein said tip support including a pair of opposing slots at a distal end thereof for rotatably receiving said pulley.

6. The sliding distal component assembly of clause 1 further comprising a recess on said tip support cavity for receiving said pulley.

7. The sliding distal component assembly of clause 6 wherein said pulley is offset from the longitudinal axis of the tip support cavity.

8. The sliding distal component assembly of clause 7 wherein said sliding distal component includes an instrument on a distal end thereof that extends from said tip support cavity when said sliding distal component translates distally.

9. The sliding distal component assembly of clause 1 wherein said at least one pull wire comprises first and second discreet pull wires each having distal and proximal ends, the proximal end of the first pull wire being operably coupled to the actuation mechanism and the distal end operably coupled to a fixation point on the sliding distal component and wherein the second pull wire is operably coupled to the pulley and the distal end of the second pull wire is coupled to the fixation point and the proximal end coupled to the actuation mechanism.

10. The sliding distal component assembly of clause 1 wherein said at least one pulley comprises first and second pulleys rotatably housed within first and second recesses formed within the tip support cavity.

11. The sliding distal component assembly of clause 10 wherein said at least one pull wire comprises first, second and third pull wires each having distal and proximal ends, the proximal end of said first pull wire operably coupled to said actuation mechanism and the distal end of said first pull wire operably coupled to a first fixation point on the sliding distal component, the second pull wire being operably coupled to said first pulley with the distal end coupled to a second fixation point on the sliding distal component and the proximal end operably coupled to the actuation mechanism, the third pull wire being operably coupled to said second pulley with the distal end coupled to a third fixation point on the sliding distal component and the proximal end operably coupled to the actuation mechanism.

12. The sliding distal component assembly of clause 1 wherein said at least one pulley comprises first and second pulleys, said first pulley being rotatably housed within a first recesses formed within the tip support cavity, said second pulley being coupled to said sliding distal component and rotatably received by opposing channels formed within the tip support cavity.

13. The sliding distal component assembly of clause 1 wherein said tip support cavity includes first and second opposing channels and further wherein said sliding distal component includes a first pin portion received by said first channel and a second pin portion received by said second channel and further wherein said tip support cavity includes first and second receiving slots at a distal end thereof.

14. The sliding distal component assembly of clause 13 wherein said pulley includes first and second pins on opposing sides thereof received by said first and second receiving slots.

15. The sliding distal component assembly of clause 14 further comprising an upper linkage bar operably coupled to said first sliding distal component pin portion and a lower linkage bar operably coupled to said second sliding distal component pin portion.

16. The sliding distal component assembly of clause 15 further comprising an upper jaw having an elongate arm operably coupled to said upper linkage bar by an upper linkage bar pin at a first position and operably coupled to said first pulley pin at a second position.

17. The sliding distal component assembly of clause 16 further comprising a lower jaw having an elongate arm operably coupled to said lower linkage bar by a lower linkage bar pin at a first position and operably coupled to said second pulley pin at a second position.

18. The sliding distal component assembly of clause 17 wherein said upper and lower jaws are operably coupled with each other at a common point of rotation by said pulley.

19. The sliding distal component assembly of clause 17 wherein said upper and lower jaws are in the closed position when the sliding distal component assembly is configured to translate proximally.

20. The sliding distal component assembly of clause 17 wherein said upper and lower jaws are in the open position when the sliding distal component is configured to translate distally.

The features of the invention will now be described in detail with reference to the accompanying Figures.

BRIEF DESCRIPTION OF THE DRAWINGS

For a better understanding of the invention, and to show how the same may be carried into effect, reference will now be made, by way of example, to the accompanying drawings, in which:

FIGS. 10A-10B are perspective and side views, respectively, of the sliding distal component assembly in accordance with the invention.

DETAILED DESCRIPTION OF THE INVENTION

Figure 1:
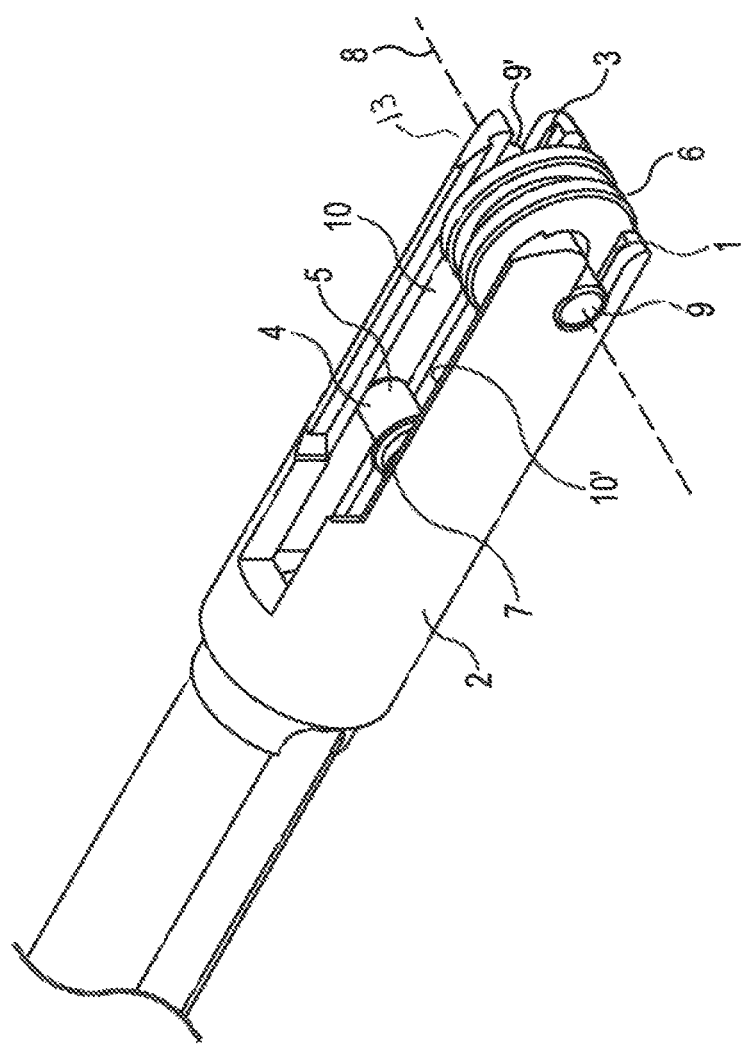
FIG. 1 is a perspective view of a sliding distal component assembly utilizing a pulley that is mounted at the distal end and along the longitudinal axis of a tip support in accordance with the invention.

Referring now to FIGS. 1-2C the sliding distal component assembly 100 broadly includes a tip support 2, a sliding distal component 4, a pulley 6, and pull wire 12. The tip support 2 is positioned at the distal tip of a catheter 15 and defines a cavity 17 therewithin that houses the various components of the sliding distal component assembly 100.

Catheter 15 may be deflectable or contain a fixed curve design of various shapes, and may vary in size depending on the specific application. The sliding distal component 4 includes a pair of opposing pins 5, 7 which are received by a pair of opposing channels 10, 10' disposed within the tip support cavity 17 to enable the sliding distal component 4 to translate proximally or distally relative to the longitudinal axis of the tip support 2. Pulley 6 includes pins 9, 9' which are received in slots 1, 3 at the distal end 13 of the tip support 2 and configured to rotate freely around pulley axis 8 but pulley 6 does not translate in relation to the tip support 2. Pulley 6 is positioned distal to the sliding distal component 4.

Figure 2A:
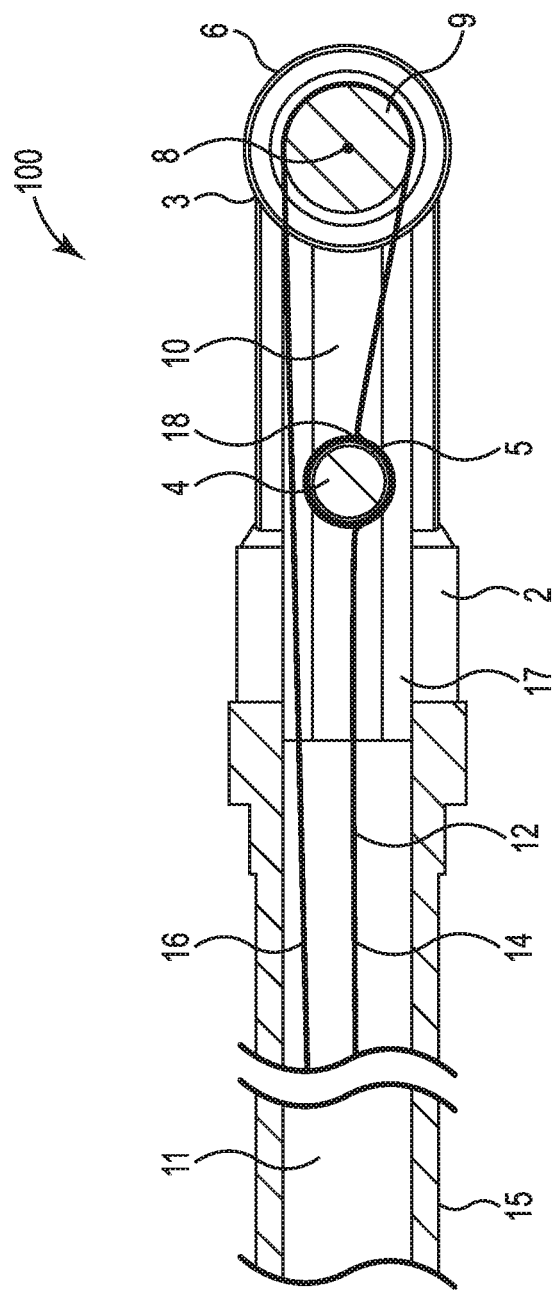
FIG. 2 is a sectional view showing how the pull wire is routed in the sliding distal component assembly shown in FIG. 1.
Figure 4:
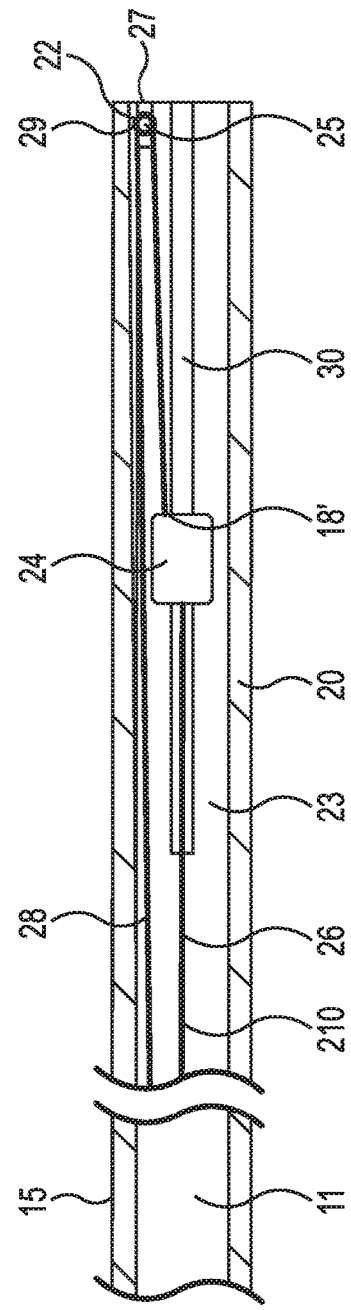
FIG. 4 is a sectional view showing how the pull wire is routed in the sliding distal component assembly shown in FIG. 3.
Figure 6:
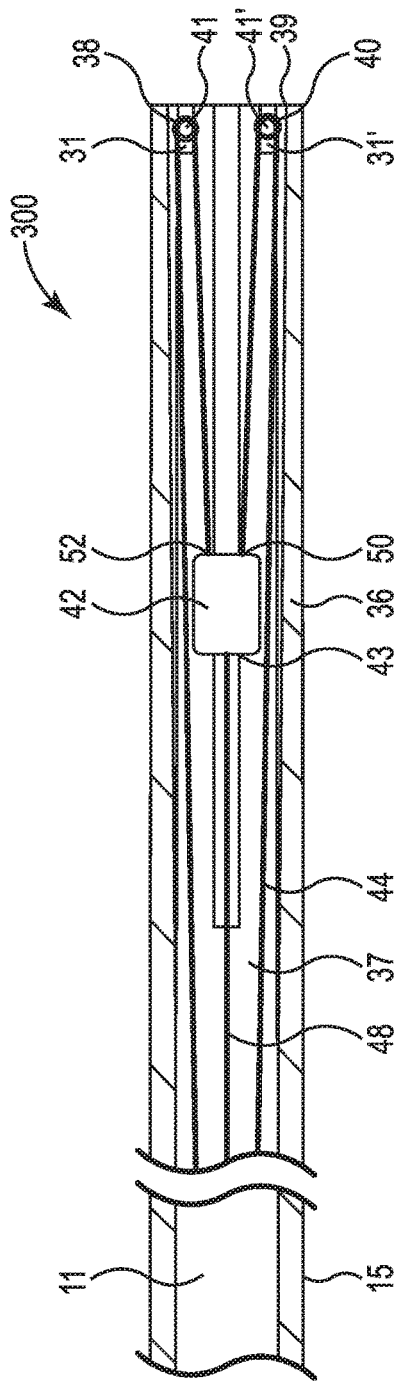
FIG. 6 is a sectional view showing how the pull wire is routed in the sliding distal component assembly shown in FIG. 5.
Figure 8:
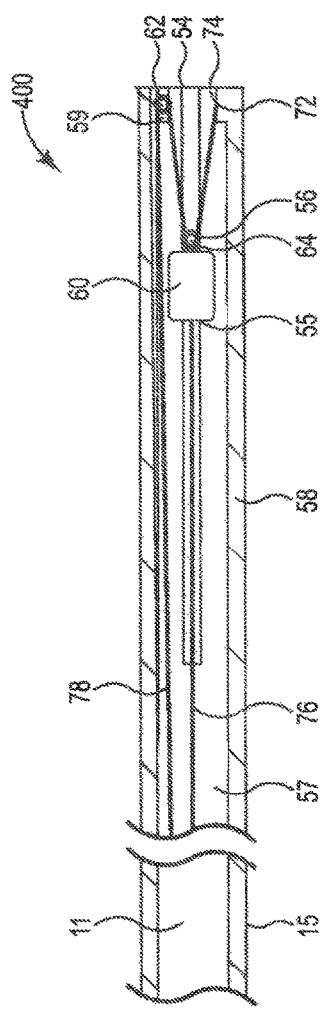
FIG. 8 is a sectional view showing how the pull wire is routed in the sliding distal component assembly tip support shown in FIG. 7.

Referring now to FIG. 2A, a sectional view of the sliding distal component assembly 100 of FIG. 1 is shown. Pull wire 12 includes a first section 14 and a second section 16. A proximal end of first section 14 of pull wire 12 is coupled to an actuation mechanism such as a pull trigger, slide button, or other mechanisms known to those of skill in the art operably coupled to catheter 15. For example, actuation mechanism may include the control handle disclosed in U.S. Pat. No. 9,138,561, which is hereby incorporated by reference in its entirety. First section 14 is coupled to and extends from the actuation mechanism distally through the catheter lumen 11 into the tip support cavity 17, where it is coupled to the sliding distal component 4 at a fixation point 18. Those of skill in the art will appreciate that although the sliding distal component of FIGS. 1 and 2A-2C is depicted as being circular it may have other shapes such as square (as seen in FIGS. 4, 6 and 8), cylindrical, elliptical and the like.

The coupling at the fixation point 18 may be by mechanical means such as welding or soldering or by chemical means such as chemical bonding or adhesive. Those of skill in the art will appreciate that the coupling may extend wholly or partially around the circumference of the sliding distal component 4 (in the case of a circular or cylindrical sliding distal component) or may be at a single fixation point (in the case of circular, cylindrical, square and other shapes) or the coupling may also be along a portion of the perimeter of the sliding distal component (in the case of a square or other shape).

The second pull wire section 16 starts at the fixation point 18 and extends distally to pulley 6 and wound around pulley 6 and extends back proximally through the tip support cavity 17 into the catheter lumen 11 to the proximal end of the catheter where it is coupled to an actuation mechanism such as a pull trigger, slide button, or other mechanisms known to those of skill in the art. Those of skill in the art will appreciate that the single pull wire 12 having two sections 14, 16 can be replaced with two separate pull wires which are routed and fixed in the same manner.

Referring to FIG. 2B, when the actuator mechanism is actuated by a user into a first position, tension is placed on the proximal end of the first pull wire section 14 while tension is released on the proximal end of the second pull wire section 16 causing the sliding distal component 4 to translate proximally within the tip support cavity 17.

Referring to FIG. 2C, when the actuator mechanism is actuated by a user in a second position, tension is placed on the proximal end of the second pull wire section 16 while tension is released on the proximal end of the first pull wire section 14 causing the sliding distal component 4 to translate distally within the tip support cavity 17.

Figure 3:
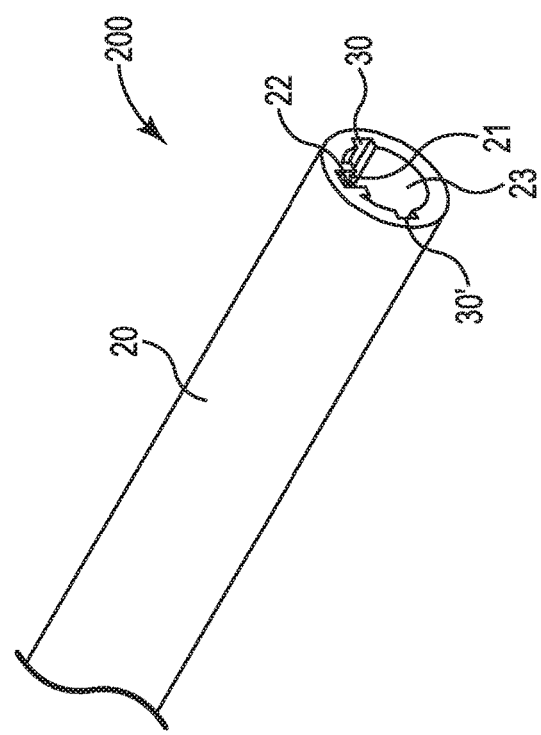
FIG. 3 is a perspective view of a sliding distal component assembly utilizing a single, miniature pulley that is mounted at the distal end of and positioned off the longitudinal axis of a tip support in accordance with the invention.

Referring to FIG. 3, a perspective view of another aspect of the sliding distal component assembly 200 is shown in which pulley 22 has a diameter that is smaller than the internal diameter of the tip support cavity 17 enabling pulley 22 to be offset from the longitudinal axis of the tip support 20 in recess 21. Tip support cavity 23 also includes opposing channels 30, 30' which receive pins (not shown) positioned on the sliding distal component 24 allowing it to translate distally and proximally. Similar to pulley 6, pulley 22 includes opposing pins thereon. Recess 21 includes channels (not shown) that receive opposing pulley pins allowing pulley 22 to rotate about its axis 25.

Referring to FIG. 4, a sectional view of the sliding distal component assembly 200 of FIG. 3 is shown. The tip support 20 defines a tip support cavity 23 that houses the various components comprising the sliding distal component assembly 200 including pulley 22. As depicted, the sliding distal component 24 is square. However, those of skill in the art will appreciate that the sliding distal component may be of any shape such as circular, cylindrical, elliptical and the like. Sliding distal component 24 is disposed within and opposing pins (not shown) engage opposing channels 30, 30' in the tip support cavity 23 enabling it to translate proximally or distally relative to the longitudinal axis of the tip support 20. Pulley 22 is coupled within the tip support cavity 23 at the distal end 27 of the tip support 20 in recess 21. Pulley 22 includes opposing pins thereon. Recess 21 includes channels (not shown) that receive opposing pulley pins allowing pulley 22 to rotate freely around pulley axis 25 but not translate linearly in relation to the tip support 20.

Pull wire 210 includes a first pull wire section 26 and a second pull wire section 28. The first pull wire section 26 is coupled to an actuation mechanism at the distal end of catheter 15 proximal to the sliding distal component 24. First pull wire section 26 extends distally through the catheter lumen 11 into the tip support cavity 23, where it is wound around and coupled to the sliding distal component 24 at a fixation point 18'. The coupling at the fixation point 18' may be by mechanical means such as welding or soldering or by chemical means such as chemical bonding or adhesive. Those of skill in the art will appreciate that the coupling may be at a single fixation point, multiple fixation points or the coupling/fixation point may extend continuously along a portion of the perimeter of sliding distal component 24. The second pull wire section 28 starts at the fixation point 18 and extends distally to pulley 22, wound around pulley 22 and extends back proximally through the tip support cavity 23 into the catheter lumen 11 to the proximal end of the catheter 15 where it is coupled to an actuation mechanism (not shown) such as a pull trigger, slide button, or other mechanisms known to those of skill in the art including that disclosed in U.S. Pat. No. 9,138,561 incorporated by reference herein in its entirety. In routing the second pull wire section 28 proximally to the actuation mechanism, it does not contact sliding distal component 24. Those of skill in the art will appreciate that the single pull wire 210 having two sections 26, 28 may be replaced with two separate pull wires which are routed and fixed in the same manner.

When the actuator mechanism is actuated by a user into a first position, tension is placed on the proximal end of the first pull wire section 26 while tension is released on the proximal end of the second pull wire section 28 causing the sliding distal component 24 to translate proximally within the tip support cavity 23. When the actuator mechanism is actuated by a user into a second position, tension is placed on the proximal end of the second pull wire section 28 while tension is released on the proximal end of the first pull wire section 26 causing the sliding distal component 24 to translate distally within the tip support cavity 23.

The advantage of the smaller diameter and off-axis positioned pulley 22 is that the sliding distal component 24 may be coupled to an instrument, by way of example a needle cannula, on the distal end thereof that will be housed within the tip support cavity 23 when the sliding distal component 24 is in a proximal position and extend out of the tip support cavity 23 to a surgical site when the sliding distal component 24 translates to a distal position.

Figure 5:
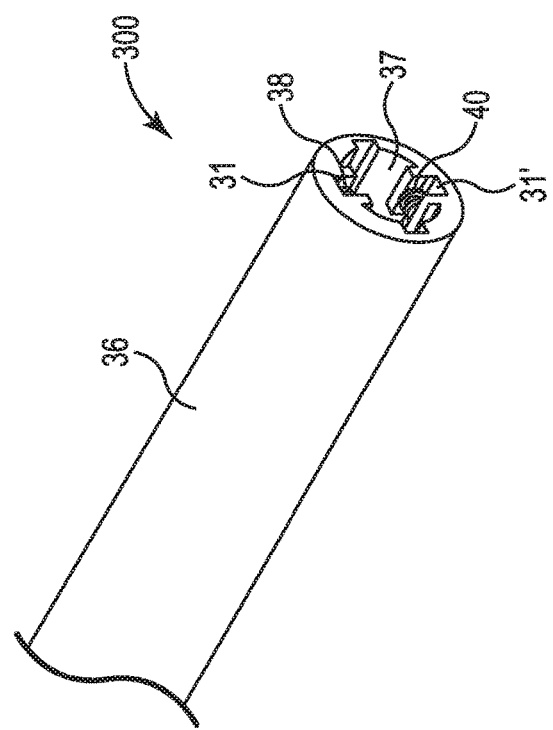
FIG. 5 is a perspective view of a sliding distal component assembly utilizing dual, miniature pulleys positioned off the longitudinal axis of a tip support and diametrically opposing one another in accordance with the invention.

Referring now to FIGS. 5 and 6, sliding distal component assembly 300 broadly includes tip support 36 defining tip support cavity 37 therewithin, sliding distal component 42, pulleys 38, 40 and pull wires 44, 46, 48. Tip support cavity 37 is configured to house the various components of the sliding distal component assembly 300. Pulleys 38, 40 each have diameters that are smaller than an internal diameter of the tip support 36. Each of pulleys 38, 40 include a pair of opposing pins (not shown). Pulleys 38, 40 are positioned in recesses 31, 31' in tip support cavity 37 opposite each other and offset from the longitudinal axis of the tip support 36. Opposing pins on pulleys 38, 40 are received by a channel in each recess 31, 31' that allow pulleys 38, 40 to rotate about their respective axis.

Sliding distal component 42 is configured to be disposed within and engage the tip support 36 cavity so that it is able to translate proximally or distally relative to the longitudinal axis of the tip support 36. Sliding distal component 42 is depicted as having a square shape but as discussed hereinbefore may have any shape including circular, cylindrical or the like.

Pulleys 38, 40 include a pair of opposing pins (not shown) that are coupled to recesses 31, 31' within tip support cavity 37 proximate the distal end 39 of tip support 36 such that they may rotate freely around each respective pulley axis 41, 41' but cannot translate linearly in relation to the tip support 36. A proximal end of first pull wire 48 is coupled to an actuation mechanism operably coupled to catheter 15. From the actuation mechanism pull wire 48 extends distally through catheter lumen 11 into the tip support cavity 37, where it is coupled to sliding distal component 42 at fixation point 43. The coupling at the fixation point 43 may be by mechanical means such as welding or soldering or by chemical means such as chemical bonding or adhesive. Those of skill in the art will appreciate that the coupling may be a single point but may also extend along a portion of the perimeter of sliding distal component 42.

Second pull wire 44 is coupled to second fixation point 50 on sliding distal component 42 and extends distally to pulley 40 where it wraps around pulley 40 then extends proximally through the tip support cavity 37 into the catheter lumen 11 to the proximal end of the catheter 15 where it is coupled to an actuation mechanism such as a pull trigger, slide button, or other mechanisms known to those of skill in the art. In routing the second pull wire 44 proximally to the actuation mechanism, it does not contact sliding distal component 42.

Third pull wire 46 begins at third fixation point 52 on sliding distal component 42 and extends distally to pulley 38, wraps around pulley 38 and then extends proximally through tip support cavity 37 into catheter lumen 11 to the proximal end of the catheter 15 where it couples to the actuation mechanism. In routing the third pull wire 46 proximally to the actuation mechanism, it does not contact sliding distal component 42.

When the actuator mechanism is actuated by a user to a first position, tension is placed on the first pull wire 48 while tension is released on the proximal ends of the second and third pull wires 44, 46 causing sliding distal component 42 to translate proximally within the tip support 36 cavity. When the actuator mechanism is actuated by a user to a second position tension is placed on second and third pull wires 44, 46 while tension is released on the first pull wire 48 causing the sliding distal component 42 to translate distally within the tip support cavity 37.

An advantage of the smaller diameter and off-axis positioned pulleys 38, 40 is that the sliding distal component 42 can couple to an instrument, by way of example as a needle cannula, on its distal end that will be housed within the tip support cavity 37 when the sliding distal component 42 is in a proximal position and extend out of the tip support cavity 37 to a surgical site when the sliding distal component 42 translates to a distal position. An advantage of using second and third pull wires 44, 46 to impart distal translation to the sliding distal component 42, is that more force can be applied to the sliding distal component 42 than with a single pull wire. Having second and third pull wires 44, 46 may be helpful in situations where the sliding distal component 42 includes an instrument, such as a needle cannula, that needs to penetrate fibrous tissue, such as left ventricular scar tissue resulting from myocardial infarction.

Figure 7:
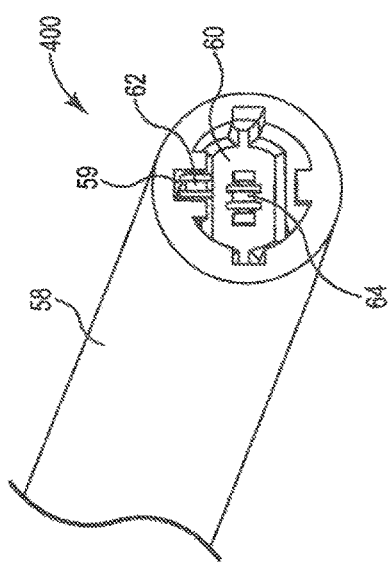
FIG. 7 is a perspective view of a sliding distal component assembly utilizing dual, miniature pulleys; one pulley is mounted to and off the longitudinal axis of a tip support, and the other pulley is mounted to the sliding distal component.

Referring to FIGS. 7 and 8 another aspect of the sliding distal component assembly 400 is depicted. Sliding distal component assembly 400 broadly includes tip support 58 defining a tip support cavity 57, first and second pull wires 76, 78, sliding distal component 60 and pulleys 62, 64. Pulleys 62, 64 have diameters that are smaller than the internal diameter of tip support 58. Tip support cavity 57 is configured to house the various components of sliding distal component assembly 400 and includes recess 59. First pulley 62 is coupled to tip support 58 proximate the distal end 54 of tip support 58 and is offset from the longitudinal axis of tip support 58 by being positioned in recess 59, as hereinbefore disclosed. Second pulley 64 is coupled to sliding distal component 60.

Sliding distal component 60 is configured to be disposed within and engage the tip support 58 cavity such that is it able to translate proximally or distally relative to the longitudinal axis of the tip support 58. First pulley 62 is coupled to tip support 58 proximate the distal end 54 of tip support 58 such that it may rotate freely around its axis 55 but cannot translate linearly in relation to the tip support 58. The second pulley 64 is coupled to the distal end of the sliding distal component 60 such that it may rotate freely around its axis 56 but cannot translate linearly in relation to the tip support 58.

A proximal end of the first pull wire 76 is coupled to an actuation mechanism operably coupled to catheter 15. From the actuation mechanism, pull wire extends distally through a catheter lumen 11 into the tip support cavity 57, where it is coupled to first fixation point 55 on sliding distal component 60. Second pull wire 56 is coupled to second fixation point 72 on tip support 58 proximate the distal end 54 thereof. From second fixation point 72, second pull wire extends proximally and wraps around second pulley 64, reverses direction and extends distally to and wraps around first pulley 62 reversing direction and extending proximally through the tip support cavity 57 avoiding contact with the sliding distal component 60 and into the catheter lumen 11 to the actuation mechanism to which it is operably coupled.

When the actuator mechanism is actuated by a user to a first position, tension is placed on first pull wire 76 while tension is released on second pull wire 78 causing the sliding distal component 60 to translate proximally within the tip support cavity 57. When the actuator mechanism is moved to a second position, tension is placed on the second pull wire 78 while tension is released on the first pull wire 76 causing the sliding distal component 60 to translate distally within the tip support cavity 57.

One advantage of having second pulley 64 coupled directly to sliding distal component 60 is that an even load distribution is applied to the sliding distal component 60 and this prevents the sliding distal component from pulling to one side or another. Moreover, the invention as depicted in FIGS. 7 and 8 also enables a 2:1 movement ratio of the sliding distal component 60 as compared to the amount of translation of the proximal end of the second pull wire 78.

One advantage of the smaller diameter and off-axis positioned pulley 62 is that the sliding distal component 60 can include an instrument (in addition to pulley 64), by way of example a needle cannula, on the distal end thereof that will be housed within the tip support cavity when the sliding distal component 60 is in a proximal position but can extend beyond the distal edge of the tip support 58 when the sliding distal component 60 translates to a distal position.

Referring generally to FIGS. 9-12 a bioptome mechanism that incorporates the sliding distal component assembly of FIGS. 1-2C is depicted. Those of skill in the art will appreciate that any of the sliding distal component assemblies described herein may be utilized and the sliding distal component assembly of FIGS. 1-2C is provided by way of example and not of limitation. A bioptome is a medical device that is traditionally employed to sample tissue, for example during biopsies. The traditional bioptome includes a 4-bar linkage system that is actuated via an elongate, relatively stiff rod. The bioptome in accordance with the invention has a 4-bar linkage system articulated through a pulley system by the application of tension to pull wires.

Figure 9:
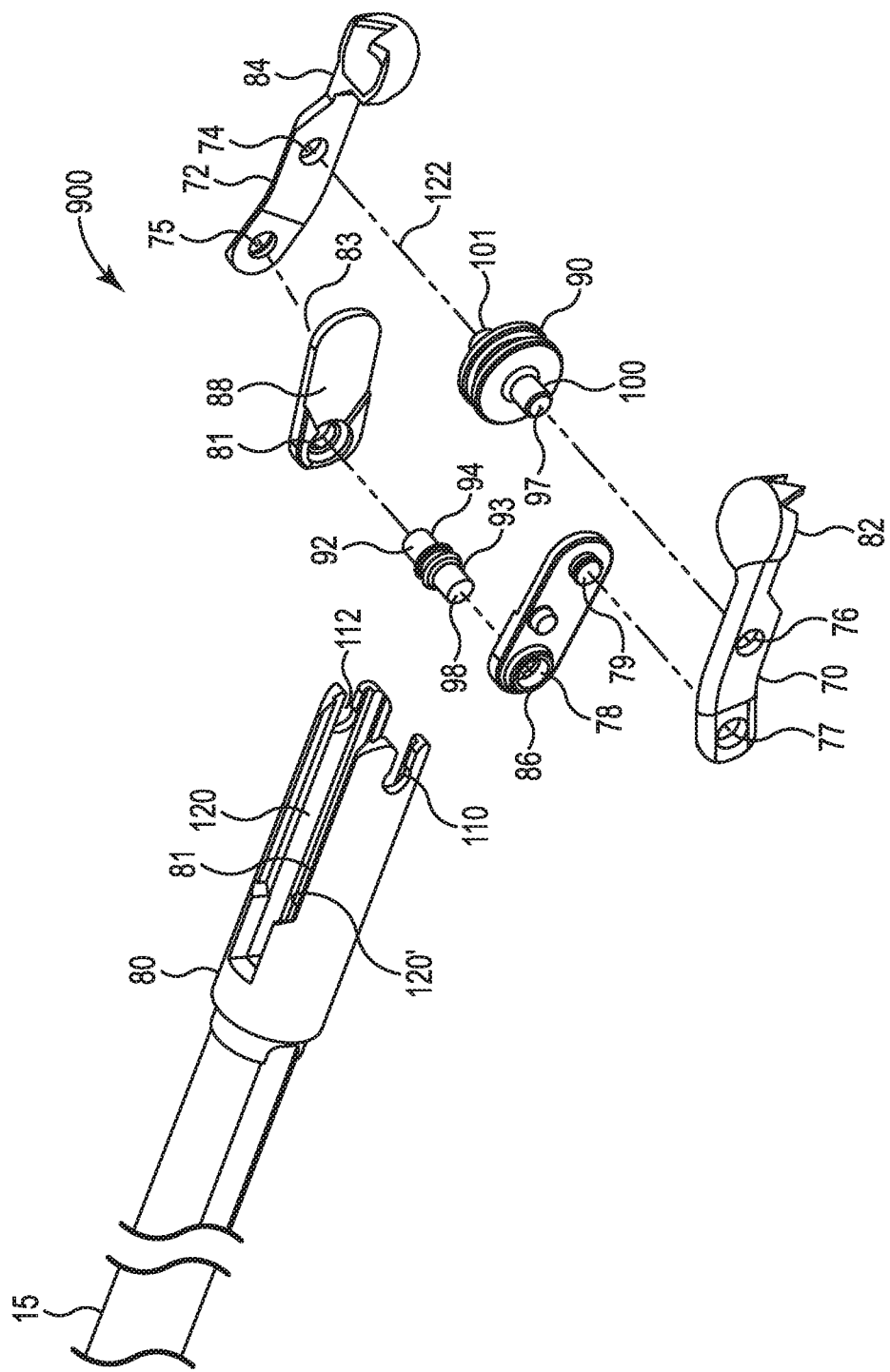
FIG. 9 is an exploded view of a sliding distal component assembly utilizing a single pulley mounted along the longitudinal axis of the tip support in combination with an integrated linkage system where two of the linkages form pinching jaws to create a bioptome catheter tip.

Referring to FIG. 9 an exploded view of the bioptome mechanism 900 is depicted. Bioptome mechanism 900 includes upper jaw 82, lower jaw 84 and a four bar linkage system, hereinafter described. Upper and lower jaws 82, 84 include elongate arms 70, 72 having receiving holes 74, 75, 76 and 77, respectively. Sliding distal component 92 includes first and second pin portions 93, 94.

Upper jaw includes receiving holes 76, 77 on elongate arm 70. Upper linkage bar 86 includes receiving hole 78 and upper linkage bar pin 79. Upper jaw 82 is coupled to the upper linkage bar by upper linkage bar pin 79. Hole 78 receives sliding distal component pin portion 93. Upper linkage bar pin 79 is received by hole 77 on elongate arm 70. Pulley pin 100 is received by upper jaw receiving hole 76.

Lower jaw includes receiving holes 75, 75 on elongate arm 72. Lower linkage bar 88 includes receiving hole 81 and lower linkage bar pin 83. Lower jaw 84 is coupled to the lower linkage bar 88 by lower linkage bar pin 83. Hole 81 of lower linkage bar 88 receives sliding distal component second pin portion 94. Pulley pin 101 is received by lower jaw receiving hole 74.

Distal pulley wheel 90 includes first and second pin portions 100, 101. First pin portion 100 is received by hole 76 in elongate arm 70. Second pin portion 101 is received by hole 74 in elongate arm 72. Pin portions 100, 101 are received by slots 110, 112 in tip support 80 which allow distal pulley wheel 90 to rotate about its axis 122.

Thus, the four bar linkage system includes four connection points. The first connection point is a pinned connection at which point the upper and lower jaws 82, 84 couple with each another at a common point of rotation created by the distal pulley wheel 90. The upper and lower jaws 82, 84 rotate about the mating pins 100, 101 on the distal pulley wheel 90. The distal pulley wheel 90 rotates about pin axis 97, but is otherwise fixed in all three translation directions (X Y, Z in three-dimensional space) with respect to the tip support 80.

The second connection point forming the four bar linkage system is the coupling of the upper jaw 82 with the upper linkage bar 86. The second connection is a pinned mating connection that is formed by upper linkage bar pin 79 and the receiving hole 77 in the upper jaw 82 elongate arm 70. The upper jaw 82 and upper linkage bar 86 rotate about the foregoing pined mating connection 79/77.

The third connection point forming the four bar linkage system is the coupling of the lower jaw 84 and the lower linkage bar 88. The third connection is a pinned mating connection that is formed by the lower linkage bar pin 83 and the lower jaw receiving hole 75 in the elongate arm 72 of lower jaw 84. The lower jaw 84 and the lower linkage bar 88 rotate about the pined mating connection 83/75.

The fourth connection point forming the four bar linkage system is at the proximal ends of the upper and lower linkage bars 86, 88. The fourth connection is formed by the sliding distal component 92 having first and second pin portions 93, 94 which are received by upper and lower bar receiving holes 78, 81 respectively creating a pinned connection between the two linkage bars 86, 88. The fourth connection point also forms a keyed mating arrangement with the tip support 80 when first and second pin portion 93, 94 are received by channels 120, 120' in tip support cavity 81 allowing the sliding distal component pin 92 to rotate in relation to its pin axis 98 and translate in the proximal or distal direction in relation to the longitudinal axis of the tip support 80. The sliding distal component pin 92 and fourth connection point are restricted from translation in axial directions that are orthogonal to the longitudinal axis of the tip support 80. When the sliding distal component pin 92 translates distally the jaws 82, 84 are opened. When the sliding distal component pin 92 translates proximally, the jaws 82, 84 are closed.

Figure 10A:
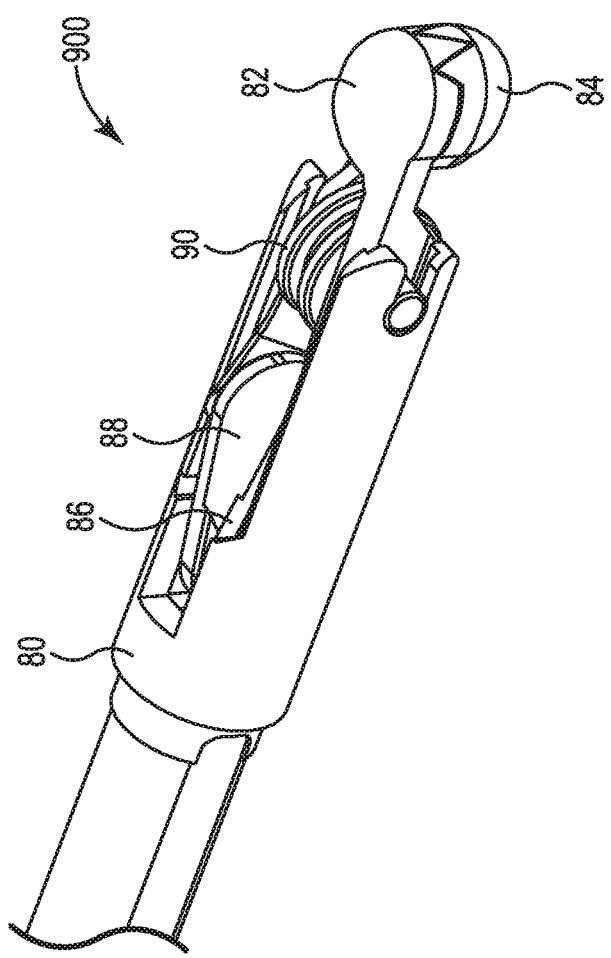

FIG. 10A is a perspective view of the assembly shown in FIG. 9 with the jaws closed. FIG. 10B is a perspective view of the assembly shown in FIG. 9 with the jaws open.

Figure 11:
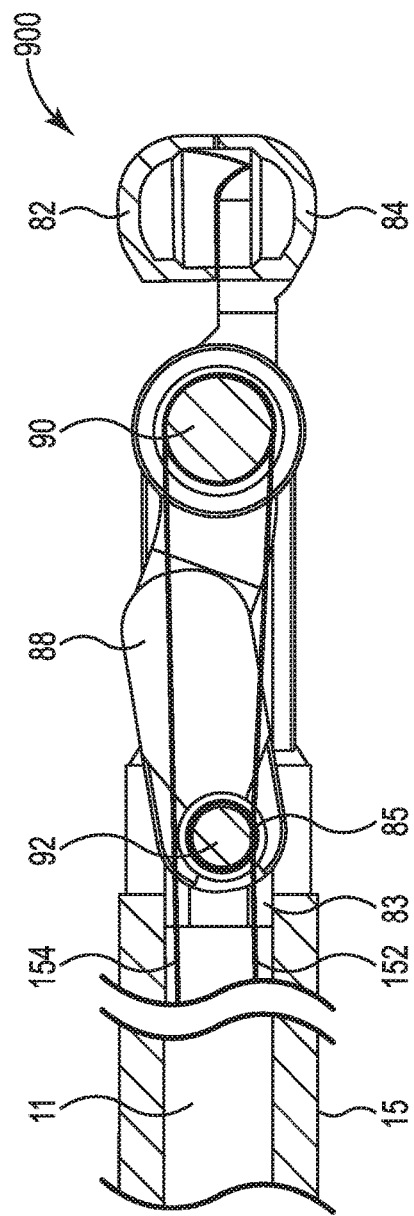
FIG. 11 is a sectional view of a sliding distal component assembly with an integrated linkage system that forms a bioptome catheter tip illustrating the routing of a pull wire when the jaws are in a near-closed configuration.

Referring now to FIG. 11, a sectional view of the bioptome assembly including a sliding distal component of FIG. 9 is depicted. The proximal end of first pull wire section 152 is coupled to an actuation mechanism operably coupled to catheter 15 as hereinbefore described. From the actuation mechanism, first pull wire section extends distally through the catheter lumen into the tip support cavity 83, where it is coupled to the sliding distal component pin 92 at a fixation point 85. Second pull wire section 154 commences at the fixation point 85 of the sliding distal component pin 92 and extends distally where it wraps around the distal pulley wheel 90, reverses direction, and continues back proximally through the tip support cavity 83 avoiding contact with the sliding distal component pin 92 and into the catheter lumen 11 to the proximal end of the catheter 15 where it is coupled to the actuation mechanism.

Referring to FIG. 11 when the actuator mechanism is actuated by a user to a first position, tension is placed on the first pull wire section 152 while tension is released on the proximal end of the second pull wire section 154 causing the sliding distal component pin 92 to translate proximally within the tip support cavity 83 in turn causing jaws 82, 84 to close due to the scissor action of the four bar linkage system.

Figure 12:
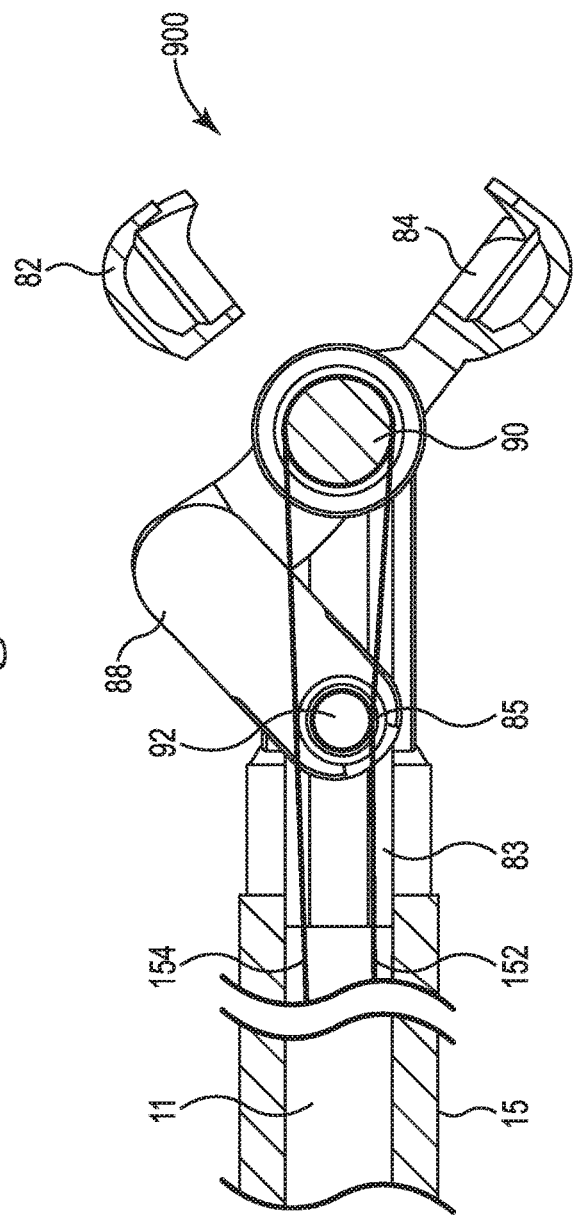
FIG. 12 is a sectional view of a sliding distal component assembly with an integrated linkage system that forms a bioptome catheter tip illustrating the routing of a pull wire when the jaws are in an open configuration.

Referring to FIG. 12, when the actuator mechanism is actuated by a user to a second position, tension is placed on second pull wire section 154 while tension is released on the first pull wire section 14 causing the sliding distal component pin 92 to translate distally within the tip support cavity 83 in turn causing jaws 82, 84 to open due to the scissor action of the four bar linkage system. Those of skill in the art will appreciate that the single pull wire having two sections 152, 154 may be replaced with two separate pull wires which are routed and fixed in the same manner and thus producing the same functional result. Those of skill in the art will also appreciate that the various sliding distal component assemblies described hereinbefore may also be utilized with the bioptome mechanism.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application. Thus, the breadth and scope of the present invention should not be limited by any of the above described embodiments. Rather, the scope of the invention should be defined in accordance with the following claims and their equivalents.

What is claimed is:

1. A sliding distal component assembly comprising:
a tubular shaft having a lumen, the tubular shaft coupled to an actuation mechanism moveable between a first position and a second position;
a tip support operably coupled to said tubular shaft and defining a tip support cavity therewithin, said tip support cavity continuous with said tubular shaft lumen;
a pulley system including a first pulley, a sliding distal component and at least one pull wire operably coupled to said first pulley and said sliding distal component, at least a portion of said pulley system being housed within said tip support cavity,
wherein when said actuation mechanism is in said first position the sliding distal component is configured to translate proximally and when said actuation mechanism is in said second position the sliding distal component is configured to translate distally,
wherein said tip support cavity includes first and second opposing channels and further wherein said sliding distal component includes a first pin portion received by said first channel and a second pin portion received by said second channel,
and wherein said assembly further comprises an upper linkage bar operably coupled to said first pin portion and a lower linkage bar operably coupled to said second pin portion.

2. The sliding distal component assembly of claim 1 wherein said at least one pull wire further comprises a first pull wire section having a distal end coupled to said sliding distal component at a fixation point and a proximal end coupled to said actuation mechanism and a second pull wire section having a distal end coupled to said fixation point and a proximal end coupled to said actuation mechanism, wherein said second pull wire section is operably coupled to said first pulley.

3. The sliding distal component assembly of claim 2 wherein said actuation mechanism is configured in the first position to apply tension to the proximal end of the first pull wire section to cause said sliding distal component to translate proximally and further wherein said actuation mechanism is configured in the second position to apply tension to the proximal end of the second pull wire section to cause said sliding distal component to translate distally.

4. The sliding distal component assembly of claim 1 wherein said tip support cavity includes a pair of opposing channels therewithin for slidably receiving said sliding distal component.

5. The sliding distal component assembly of claim 1 wherein said tip support includes a pair of opposing slots at a distal end thereof for rotatably receiving said first pulley.

6. The sliding distal component assembly of claim 1 further comprising a recess on said tip support cavity for receiving said first pulley.

7. The sliding distal component assembly of claim 6 wherein said first pulley is offset from the longitudinal axis of the tip support cavity.

8. The sliding distal component assembly of claim 7 wherein said sliding distal component includes an instrument on a distal end thereof that extends from said tip support cavity when said sliding distal component translates distally.

9. The sliding distal component assembly of claim 1 wherein said at least one pull wire comprises first and second discrete pull wires each having distal and proximal ends, the proximal end of the first pull wire being operably coupled to the actuation mechanism and the distal end operably coupled to a fixation point on the sliding distal component and wherein the second pull wire is operably coupled to the first pulley and the distal end of the second pull wire is coupled to the fixation point and the proximal end coupled to the actuation mechanism.

10. The sliding distal component assembly of claim 1 wherein said first pulley and a second pulley are rotatably housed within first and second recesses formed within the tip support cavity.

11. The sliding distal component assembly of claim 10 wherein said at least one pull wire comprises first, second and third pull wires each having distal and proximal ends, the proximal end of said first pull wire operably coupled to said actuation mechanism and the distal end of said first pull wire operably coupled to a first fixation point on the sliding distal component, the second pull wire being operably coupled to said first pulley with the distal end coupled to a second fixation point on the sliding distal component and the proximal end operably coupled to the actuation mechanism, the third pull wire being operably coupled to said second pulley with the distal end coupled to a third fixation point on the sliding distal component and the proximal end operably coupled to the actuation mechanism.

12. The sliding distal component assembly of claim 1 wherein said first pulley is rotatably housed within a first recesses formed within the tip support cavity, and a second pulley is coupled to said sliding distal component and rotatably received by opposing channels formed within the tip support cavity.

13. The sliding distal component assembly of claim 1 wherein said tip support cavity includes first and second receiving slots at a distal end thereof.

14. The sliding distal component assembly of claim 13 wherein said first pulley includes first and second pulley pins on opposing sides thereof received by said first and second receiving slots.

15. The sliding distal component assembly of claim 1 further comprising an upper jaw having an elongate arm operably coupled to said upper linkage bar by an upper linkage bar pin at a first position and operably coupled to said first pulley pin at a second position.

16. The sliding distal component assembly of claim 15 further comprising a lower jaw having an elongate arm operably coupled to said lower linkage bar by a lower linkage bar pin at a first position and operably coupled to said second pulley pin at a second position.

17. The sliding distal component assembly of claim 16 wherein said upper and lower jaws are operably coupled with each other at a common point of rotation by said first pulley.

18. The sliding distal component assembly of claim 16 wherein said upper and lower jaws are in a closed position when the sliding distal component is configured to translate proximally.

19. The sliding distal component assembly of claim 16 wherein said upper and lower jaws are in an open position when the sliding distal component is configured to translate distally.

* * * * *